United States Patent [19]
Gillies

[11] Patent Number: 5,338,669
[45] Date of Patent: * Aug. 16, 1994

[54] METHOD OF PRODUCING FUSION PROTEINS

[75] Inventor: Stephen D. Gillies, Hingham, Mass.

[73] Assignee: Abbott Biotech, Incorporated, Needham, Mass.

[ * ] Notice: The portion of the term of this patent subsequent to Mar. 23, 2010 has been disclaimed.

[21] Appl. No.: 916,034

[22] Filed: Jul. 17, 1992

Related U.S. Application Data

[63] Continuation of Ser. No. 810,522, Dec. 17, 1991, Pat. No. 5,196,320, which is a continuation of Ser. No. 409,889, Sep. 20, 1989, abandoned.

[51] Int. Cl.$^5$ ............ C12N 15/13; C12N 15/62
[52] U.S. Cl. .................. 435/69.1; 435/69.7; 435/252.3; 435/320.1; 536/23.4
[58] Field of Search ............ 435/69.7, 69.1, 252.3, 435/320.1; 536/23.4

[56] References Cited

U.S. PATENT DOCUMENTS

| | | | |
|---|---|---|---|
| 4,769,326 | 9/1988 | Rutter | 435/69.7 |
| 4,771,002 | 9/1988 | Gelvin | 435/122.3 |
| 4,801,536 | 1/1989 | Stahl et al. | 432/68 |
| 4,816,567 | 3/1989 | Cabilly et al. | 530/387 |

FOREIGN PATENT DOCUMENTS

| | | |
|---|---|---|
| 1217156 | 1/1987 | Canada . |
| 0171496 | 2/1986 | European Pat. Off. . |
| 0173494 | 3/1986 | European Pat. Off. . |
| 0237157 | 9/1987 | European Pat. Off. . |
| 8601533 | 3/1986 | PCT Int'l Appl. . |
| 8806630 | 9/1988 | PCT Int'l Appl. . |
| 89/09622 | 10/1989 | PCT Int'l Appl. . |

OTHER PUBLICATIONS

Science vol. 229: 1202–1207, 20 Sep. 1985, Morrison et al. Transfectomas Provide Novel Chimeric Antibodies.
Boulianne et al., *Nature*, 312:643–646 (1984).
Maxam et al., *Methods in Enzymology*, 65:499–561 (1980).
Sandri–Goldin et al., *Molecular and Cellular Biology*, 1:743–751 (1983).
Gillies et al., *Cell*, 33:717–728 (1983).
Gubler et al., *Gene*, 25:263–269 (1983).
Morrison et al., *Proc. Natl. Acad. Sci. USA*, 81:6851–8655 (1984).
Potter et al., *Proc. Natl. Acad. Sci. USA*, 81:7161–7165 (1984).
Rupp in *Large-Scale Mammalian Cell Culture* (Tolbert et al., eds. Academic Press, Inc. pp. 19–38 (1985).
Sahagan et al., *The Journal of Immunology*, 137:1066–1074 (1986).
Lui et al., *Proc. Natl. Acad. Sci. USA*, 84:3439–3433 (1987).
Mujoo et al., *Cancer Research*, 47:1104 (1987).
Von Wedel in *Commercial Production of Monoclonal Antibodies:* A Guide for Scale–Up (Seaver, ed.) Marcel Dekker, Inc. pp. 159–173 (1987).
*Nucleic Acids Res.*, A catalogue of splice junction sequences, Mount publication, 10:459–472.
Rautmann et al., *Embo J.*, 3:2021–2028 (1984).
Boss et al., *Nucleic Acids Research*, 12:3791–3805 (1984).
Chu et al., *Nature*, 298:378–382 (1981).
Brenner et al., *Proc. Natl. Acad. Sci. USA*, 86:5517–5521 (1989).
Gossler et al., *Science*, 244:463–465 (1989).

*Primary Examiner*—Robert J. Hill, Jr.
*Assistant Examiner*—John D. Ulm
*Attorney, Agent, or Firm*—Testa, Hurwitz & Thibeault

[57] ABSTRACT

Disclosed are methods of producing fusion proteins including those with dual biological activities. These methods include the provision of a first and second DNA sequence encoding a first and second polypeptide, repectively, the digestion of the first DNA sequence at a restriction site adjacent its 3' or 5' terminus, and the ligation of a linker/adapter sequence (l/a) to the restricted end of the first DNA sequence, thereby forming a cassette. The l/a includes, at one end, that portion of the first DNA sequence extending from its terminus nearest the restriction site to the restriction site, and at the other end, one side of a splice site. A eucaryotic host cell is transfected with the cassette and the second DNA sequence having, at one end, one side of a splice site compatible with the side of the splice site on the l/a. The transfected host cell is cultured to express the transfected DNA as a single chain fusion protein.

5 Claims, 7 Drawing Sheets

FIG. IA
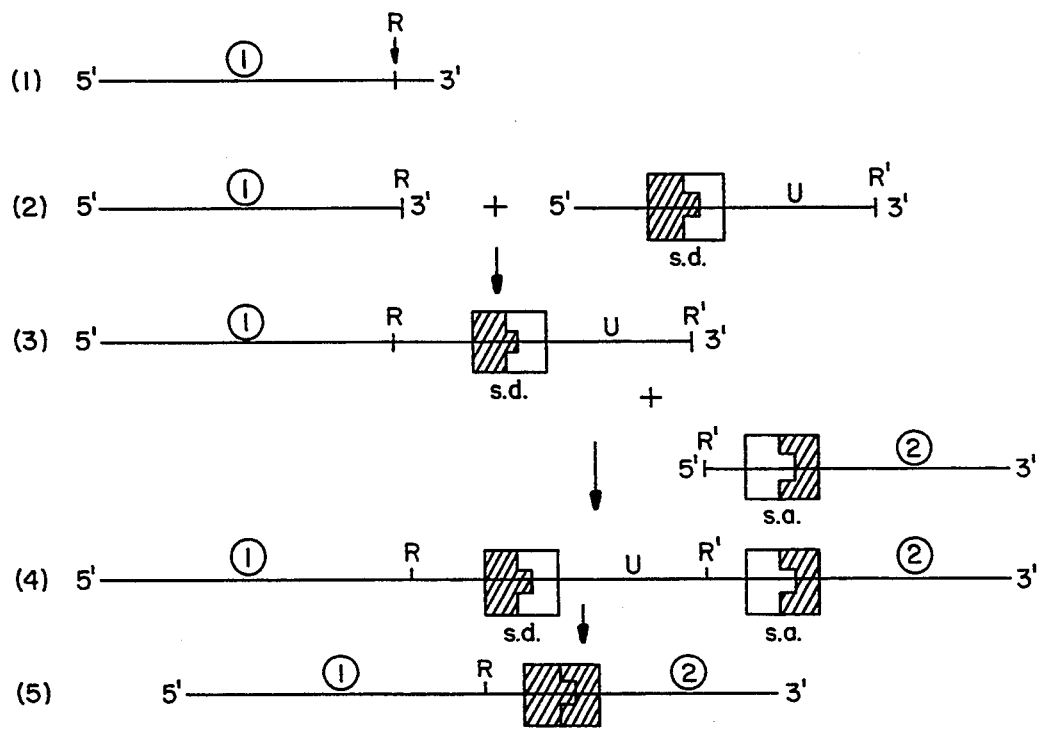
FIG. IB
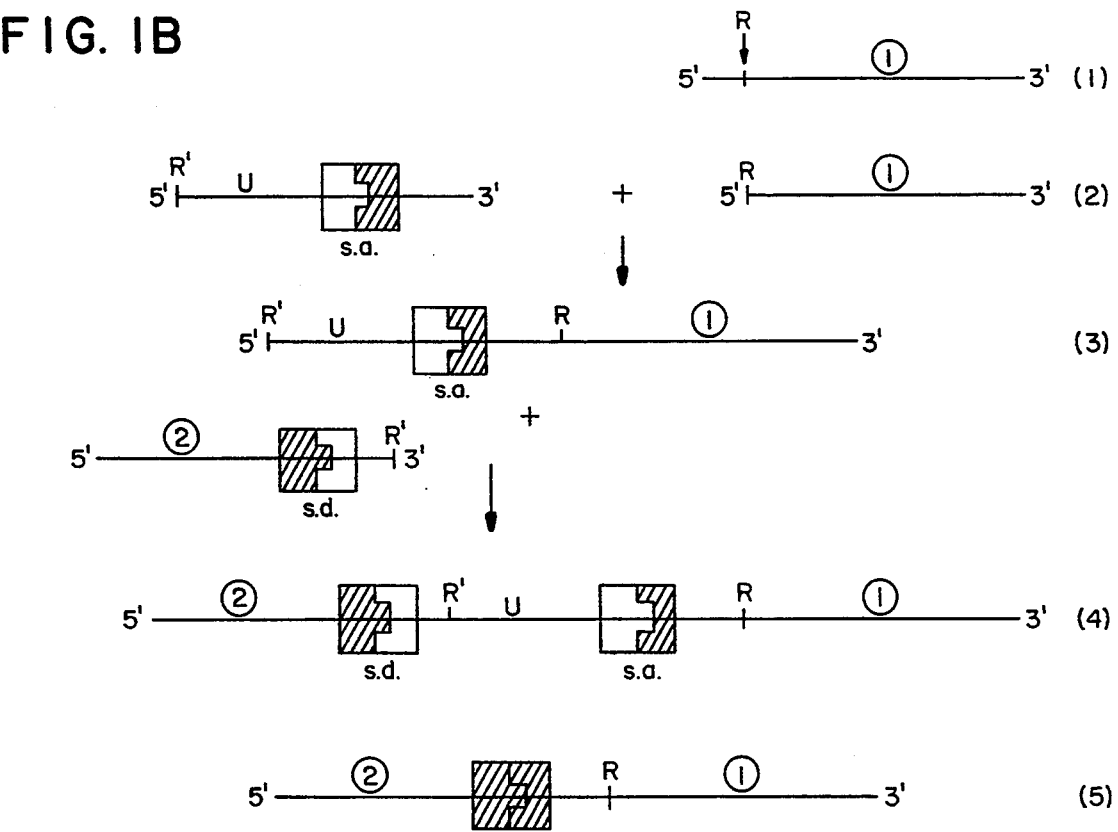

FIG. 2

```
                                                H2c
                  .         .         .         ↓         .         .
AATGTCCTCTCCACAGTCCCTGAAGACACTGACTATAACTATGGGATGGACCCTGGATCTTTATTTTAATCCTGTCGGTAACTACACAGGTGTCCACTCTGAG
                                                MetGlyTrpThrTrpIlePheIleLeuIleLeuSerValThrThrGlyValHisSerGlu
50                                              |-----------Leader----------------------|            100
                                                                                                     +1

.         .         .         .         .         .         .         .
GTCCAACTGCTGCAGTCTGGACCTGAGCTGGAGAAGCCTAGGCGCTTCTGTGATGATATCCTGAGTCAGTGATGATATCCTGCAAGGCTTCTGGTTCCTCATTCACTGGCTACAACATGA
ValGlnLeuLeuGlnSerGlyProGluLeuGluLysProSerAlaSerValMetIleSerCysLysAlaSerGlySerPheThrGlyTyrAsnMetA
          10                                    20                                      30
150                                                                                                  200

.         .         .         .         .         .         .         .
ACTGGGTGAGGCAGAACATTGGAAAGAGCCTTGAATGGATTGGAGCTATTGATCCTTACTATGGTGAACTAGCTACAACCAGAAGTTCAAGGGCAGGGC
snTrpValArgGlnAsnIleGlyLysSerLeuGluTrpIleGlyAlaIleAspProTyrTyrGlyGluLeuAlaThrThrArgSerSerArgGlnAl
                40                                      50                                      60
250                                                                                                  300

.         .         .         .         .         .         .         .
CACATTGACTGTAGACAAATCGTCCAGCAGCCTACACATGCACCTCCAAGAGCCTGACATCTGAGGACTCTGCAGTCTATTACTGTGTAAGCGGAATGGAG
aThrLeuThrValAspLysSerSerSerThrAlaTyrMetHisLeuLysSerLeuThrSerGluAspSerAlaValTyrTyrCysValSerGlyMetGlu
          70                                    80                                      90
350                                    400                                           450

|-D-|-----|
                                                                                                     500

.         .         .         .         .         .
TACTGGGGTCAAGGAACCTCAGTGACCGTCACCGTCTCCTCAGTACAACAACAGCCCATCTGTCTATCCCTTGGTCCCTGGCTGCCAGTGACACATCCGGATCC
TyrTrpGlyGlnGlyThrSerValThrValSerSerAlaThrThrAlaProSerValTyrProLeuValProGlyCysSerAspThrSerGlySer
          100
-----|    -------------------------------------------|-----------Constant Region---------------
    H4
  J
```

FIG. 3

```
           .         .         .         .         .
CAGTCTCCTCAGGCTGTGTCCTCCTCCTCAGGTTGCCTCCTCCTCAAAATGAAGTTGCCTGTGCTGTTAGGCTGTTGGTGCTGTTCTGATTCCTGCTTCCAGCAGTGATG
                                               MetLysLeuProValArgLeuLeuValLeuMetPheTrpIleProAlaSerSerAspV
                                               |-----------------Leader-----------------------| +1
          50                                  100
           .         .         .         .         .
TTGTGATGACCCAGACTCCACTCTCCCTGCCTGTCAGTCTCTTGGAGATCAAGCCTCCATCTCTTGCAGATCTAGTCAGAGTCTTGTACACCGTAATGGAAA
alValMetThrGlnThrProLeuSerLeuProValSerLeuLeuGluIleLysProProSerLeuAlaAspLeuValGlnSerLeuValHisArgAsnGlyAs
          10                  20                  30
         150                                 200
           .         .         .         .         .
CACCTATTACATTGGTACCTGCAGAAGCCAGGCCAGTCTCCAAAGCTCCTGATTCACAAAGTTTCCAACCGATTTTCTGGGGTCCCAGACAGGTTCAGT
nThrTyrLeuHisTrpTyrLeuGlnLysProGlyGlnSerProLysLeuLeuIleHisLysValSerAsnArgPheSerGlyValProAspArgPheSer
                   40                  50                  60
         250                                 300
           .         .         .         .         .
GGCAGTGGATCAGGGACAGATTTCACACTCAAGATCAGCAGAGTGGAGGCTGAGGATCTGGGAGTTTATTTCTGTTCTCAAAGTACACATGTTCCTCCGC
GlySerGlySerGlyThrAspPheThrLeuLysIleSerArgValGluAlaGluAspLeuGlyValTyrPheCysSerGlnSerThrHisValProProL
          70                  80                  90
         350                                 400
           .         .         .         .         .
TCACGTTCGGTGCTGGGACCAAGCTGGAGCTGAAACGGGCTGATGCTGCACCAACTGTATCCATCTTCCCACCATCCAGTGAGCAGTTA
euThrPheGlyAlaGlyThrLysLeuGluLeuLysArgAlaAspAlaAlaProThrValSerIlePheProProSerSerGluGlnLeu
                 100
         450
----------------|---------|-------------- Constant Region ------------
        J       K5
```

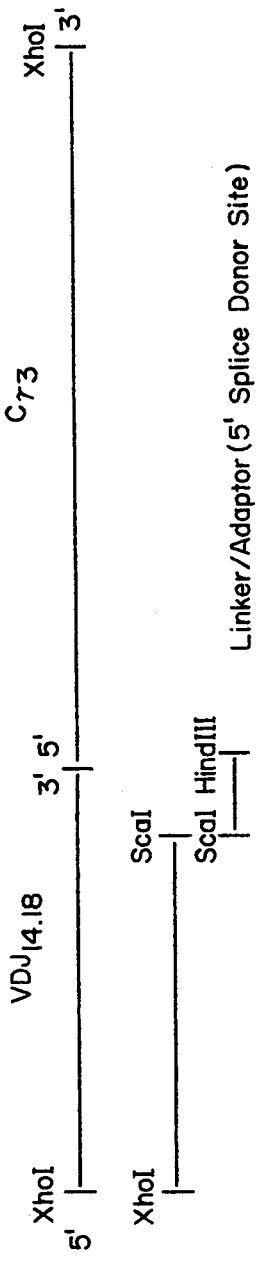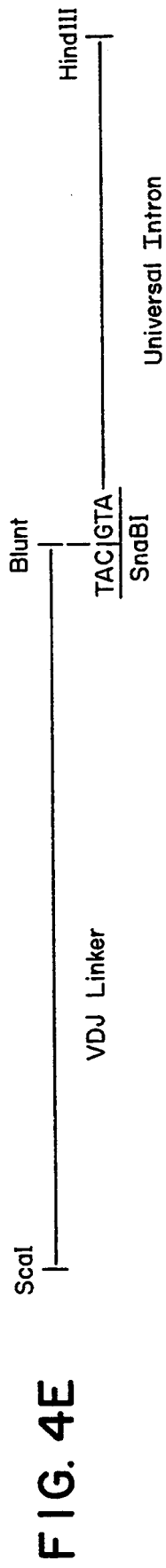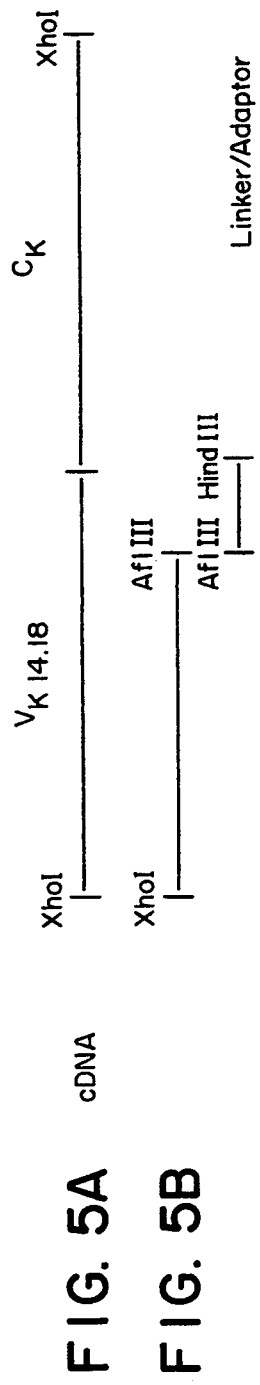
FIG. 4A
FIG. 4B
FIG. 4E
FIG. 5A
FIG. 5B

FIG. 4C

```
          5'
          Met Glu Tyr Trp Gly Gln Gly Thr Ser Val Thr Val Ser Ser Ala Thr Thr Ala         3'
        ..ATG GAG TAC TGG GGT CAA GGA ACC TCA GTC ACC GTC TCC TCA GCT ACA ACA GCC ... Murine cDNA
              ‾‾‾                                              ‾
              ScaI                                     VDJ │ C
```

FIG. 4D

```
        GAG TAC TGG GGT CAA GGA ACC TCA GTC ACC GTC TCC TCA G|GTAAGTGTGTCA // GGTAATGTCACTAAGCTT
        ‾‾‾                                                                                ‾‾‾‾‾‾
        ScaI                                                  '‾‾‾‾‾‾'                     HindIII
                                                              Splice Donor
```

FIG. 5C

```
       5'
       The His Val Pro Pro Leu Thr Phe Gly Ala Gly Thr Lys Leu Glu Leu Lys Arg Ala Asp Ala Ala
...    ACA CAT GTT CCT CCG CTC ACG TTC GGT GCT GGG ACC AAG CTG GAG CTG AAA C GG GCT GAT GCT GCA ...cDNA
               AflIII                                                    VJ
                                                                               C                    3'
```

FIG. 5D

```
A CAC GTT CCT CCG CTC ACG TTC GGT GCT GGG ACC AAG CTG GAG CTG AAA C GTAAGTGTG // GGTAATGTCACTAAGCTT
AflIII                                                              '-----'                 HindIII
                                                                    Splice Donor
```

FIG. 5E

```
 |—————————————————|————|—————————————————————|
AflIII              Blunt                    HindIII
                    TAC|GTA
                    SnaBI
     Vκ Linker              Universal Intron
```

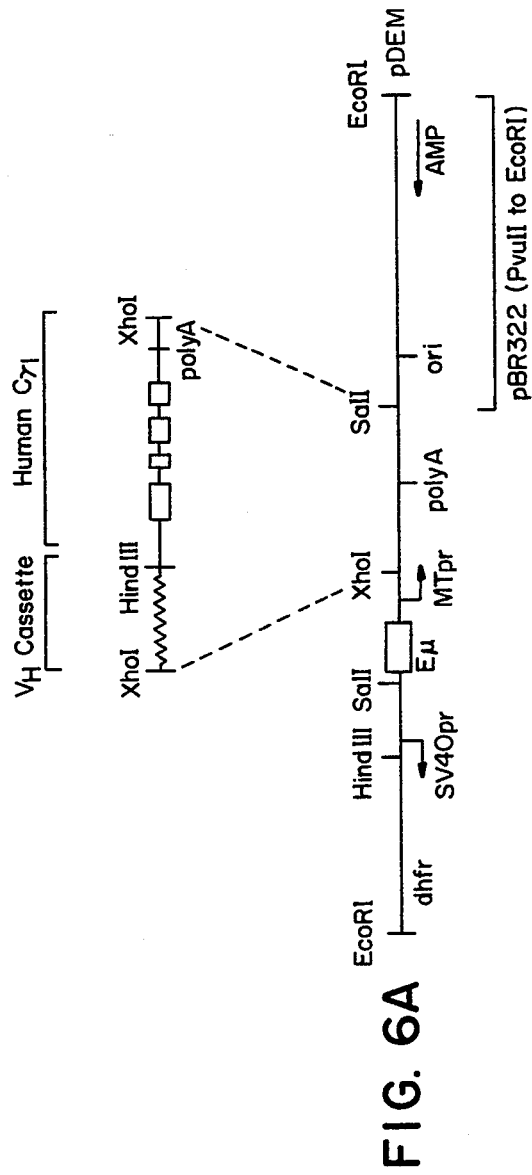
FIG. 6A
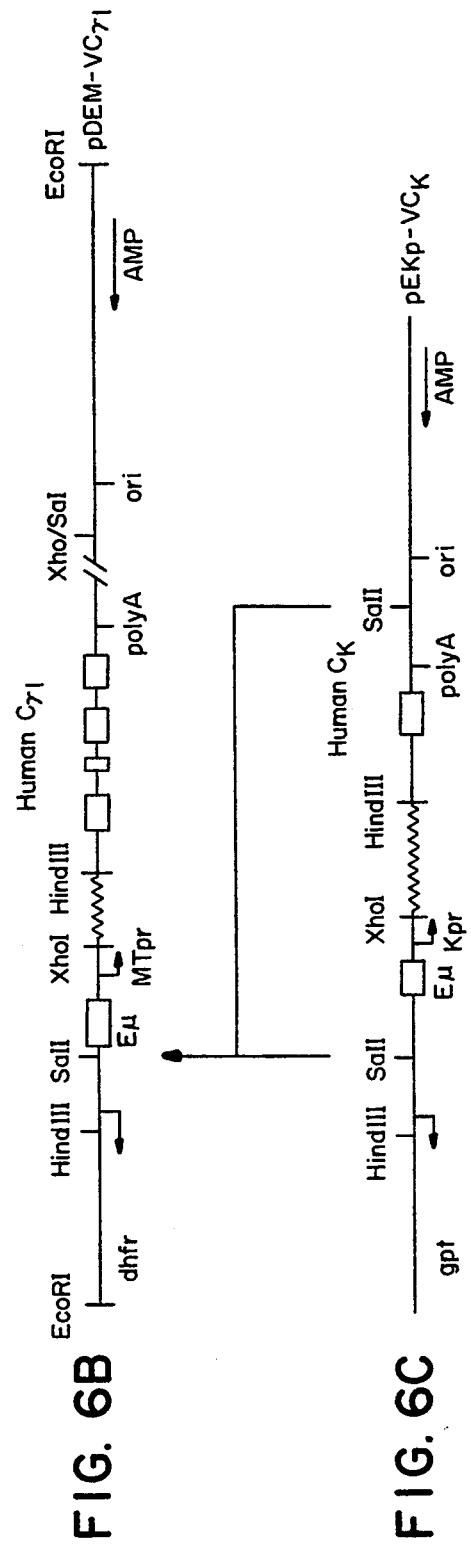
FIG. 6B
FIG. 6C

METHOD OF PRODUCING FUSION PROTEINS

This is a continuation of copending application Ser. No. 07/810,522 filed on Dec. 17, 1991 now U.S. Pat. No. 5,196,320 which was a continuation of application Ser. No. 07/409,889 filed on Sep. 20, 1989 and which is now abandoned.

BACKGROUND OF THE INVENTION

This invention relates to the production of recombinant polypeptides, and in particular, to the production of synthetic proteins having plural fused domains. More specifically, this invention relates to methods of producing recombinant fusion proteins having dual biological activities such as binding molecules and receptor proteins with preselected specificity and activity. Such fusion proteins are useful, for example, in imaging procedures, in the diagnosis and treatment of various human cancers, infectious diseases, and dysfunctions, and in the development of vaccines.

Fusion proteins having dual activities and/or functions are known and include combinations of peptide hormones, enzymes, transport and receptor proteins, viral coat proteins, interleukins, lymphokines, immunoglobulins (Igs), and fragments thereof. Some of these fusion proteins are known to provide enhanced antigenicity, and therefore, are useful in the production of vaccines. Others have high biological activity, and hence, are useful in treating various infectious and deficiency diseases and disorders. Still other fusion proteins are useful as diagnostic agents because of their enhanced targeting abilities. (See, e.g., U.S. Pat. Nos. 4,223,270, 4,801,536, CA 1217156A, WO 8806630A, and JP 63267278A for examples of such fusion proteins.)

Immunoglobulin molecules have been produced as fusion proteins (e.g., chimeric antibodies). Their structure is particularly conducive to the formation of fused polypeptides having a first protein domain (e.g., a variable region) from a first Ig molecule from one species having a particular specificity, and a second domain (e.g., a constant region) from a second Ig of a different species (and perhaps specificity). They were developed as an alternative to non-chimeric monoclonal antibodies, many of which are of non-human (e.g., murine) origin, and hence may be antigenic to humans. Human monoclonal antibodies are the most desirable therapeutic agents, as their use should provoke a greatly reduced immune response in humans. However, the production of human monoclonal antibodies by cell fusion methodologies is difficult, as immunized human spleen cells are not readily available, and as human hybridomas are notably unstable.

Chimeric antibodies composed of both human and non-human amino acid sequences should elicit less of an immune response in humans, and therefore should have improved therapeutic value. Accordingly, hybrid antibody molecules have been proposed which consist of Ig light (L) and heavy (H) chain amino acid sequences from different mammalian sources. The chimeric antibodies designed thus far comprise variable (V) regions from one mammalian source (usually murine), and constant (C) regions from human or another mammalian source (see, for example, EPO application nos. 84302368.0 (Genentech), 85102665.8 (Research Development Corporation of Japan), and 85305604.2 (Stanford University); P.C.T. application no. PCT/GB85/00392 (Celltech Limited); Morrison et al. (1984) Proc. Natl. Acad. Sci. U.S.A. 81:5851–6855; Boulianne et al. (1984) Nature 312:643–646; and Sahagan et al. (1986) J. Immunol. 137:1066–1074).

The production of recombinant chimeric antibodies with predetermined specificity has typically involved the use of cloned genomic DNA fragments. For example, the genomic DNA sequences encoding H and L chains can be cloned in their rearranged forms (i.e., in the DNA sequence that results from recombination events during B Cell maturation). As such, these genomic sequences contain the information necessary for their expression, (i.e. the 5' untranslated sequences, promoter, enhancer, protein coding region, and donor splice site). The donor splice signals at the 3' end of the V gene segments are compatible with the splice acceptor signals at the 5' end of the Ig regions of other species. That is, the splice product between the two maintains the correct reading frame. For example, when a murine V and a human $C_k$ segment are joined and transfected into the appropriate host cell type, the primary transcript is correctly spliced and results in a mature messenger RNA (mRNA) molecule with an open reading frame through both the V and C regions.

There are disadvantages to the use of genomic V region fragments for the expression of recombinant chimeric antibodies. The first involves the cloning process itself which can be quite laborious for single-copy genes, requiring the screening of many independent clones of a phage library. Furthermore, many hybridomas contain multiple rearranged V genes which represent non-productive recombinational events. The identification of the expressed $V_L$ or $V_H$ segment can often require extensive DNA sequence analysis as well as confirmation by cloning and sequencing the DNA copy of the expressed mRNA (complementary or cDNA).

A more direct approach is to clone the cDNAs for both the L and H chains, and to use cDNA expression vectors for their expression. In this case, cloning is simple and rapid, since Ig mRNA is very abundant in hybridoma cells, and highly efficient methods for cDNA cloning are available. However, when one uses this approach, a problem arises when the separate expression of different V and C regions from different Ig cDNAs is desired, as in the case of chimeric antibodies having, for example, murine V regions and human C regions. The Ig cDNA represents a direct copy of the mRNA which, in turn, is a fusion of V and C exons through normal, in vivo RNA splicing into a continuous polynucleotide sequence. Precise excision and recombination of a murine $V_H$ with a human $C\gamma_1$, for example, is not possible because appropriate restriction sites are not present at the VC junction of both sequences.

The expression of chimeric antibodies has been accomplished through the use of cloned cDNAs. This procedure may involve the mutagenesis of sequences in both the murine V region and human C region, near the VC junction, such that a common restriction site is created for directly joining the cDNA segments (Liu et al. (1987) Gene 54:33–40).

It is an object of this invention to provide a method of producing fused polypeptides. Another object is to provide methods for producing fusion proteins having dual activities and/or functions such as, for example, chimeric immunoglobulin molecules having a predetermined antigen specificity. Another object is to provide a relatively simple and rapid procedure for providing human/non-human mammalian chimetic antibodies and truncated versions thereof having reduced antigenicity in the human body. Yet another object of the invention is to provide a rapid method of producing a made-to-order chimetic immunoglobulin molecules utilizing a specifically engineered V region gene that can be attached easily to another gene, and transfected and expressed in a host cell.

SUMMARY OF THE INVENTION

The present invention provides methods of general applicability for production of fusion proteins including at least a portion of an enzyme, peptide toxin, peptide hormone, lymphokine, hormone, interleukin, and/or immunoglobulin. The invention further provides for the modification of cloned cDNAs such as Ig cDNAs so that a polypeptide such as a V region with predetermined selectivity can be expressed as an independent unit or cassette fused with any one of a variety of polypeptides such as an Ig C region from the same or a different species.

One new method involves the construction of a linker/adapter (l/a) sequence which enables the fusion of a DNA sequence encoding a first polypeptide having a naturally occurring restriction site at or near its 3' terminus, to a DNA sequence encoding a second polypeptide. The l/a sequence includes, in sequence from its 5' end, a sequence of DNA encoding the first polypeptide from a (near-)3' terminal restriction site to its 3' terminus, and a splice donor site compatible with a splice acceptor site on the 5' terminus of DNA encoding a second polypeptide. In a preferred embodiment, the l/a includes a universal intron having greater than 80 nucleotide bases in length.

To produce the fusion protein, the DNA sequence encoding the first polypeptide is digested at a suitable restriction site near the 3' end of the gene sequence. The 5' end of the l/a is then ligated to that site, thereby producing a cassette with a splice donor site at its 5' end. A eucaryotic host cell is transfected with the cassette as well as with a second DNA sequence encoding a second polypeptide and having the corresponding splice partner site (splice acceptor) at its 5' terminus. The transfected cell is then cultured to co-express the cassette and the second DNA sequence as a single chain fusion protein.

Alternatively, a first DNA sequence encoding a first polypeptide may be digested at a restriction site located 3' to and adjacent its 5' terminus, thereby producing a new 5' end of that first DNA sequence. A l/a is then ligated to the new 5' end of the first DNA sequence. This l/a includes, in sequence from its 3' end, DNA encoding that portion of the first polypeptide extending from a (near-)5' terminal restriction site to its 5' terminus, and a splice acceptor site compatible with a splice donor site on the 3' terminus of the DNA encoding a second polypeptide. In a preferred embodiment of the invention, the l/a includes greater than about 80 nucleotide bases in length.

To produce the fusion protein, the DNA encoding the first polypeptide is digested at an appropriate restriction site near the 5' end of the gene. The 3' end of the l/a is then ligated to that restricted site, thereby producing a cassette with a splice acceptor site at its 5' end. A eucaryotic host cell is transfected with the cassette as well as with a second DNA sequence encoding the second polypeptide and having the corresponding splice partner site (splice donor) at its 3' terminus. The transfected cell is then cultured to co-express the cassette and the second DNA sequence as a single chain fusion protein.

In the case of the production of chimeric antibodies, the method includes the reconstruction of a cDNA, restricted at a naturally occurring restriction site unique to the V region-encoding portion of the cDNA, by ligation of a synthetically produced DNA sequence which replaces the removed 3' terminus of the V region and adds a 3' donor splice site that mimics the donor splice site normally found on the genomic V region-encoding DNA. This V region "cassette" can be used in conjunction with any C region-encoding DNA sequence, or other protein-encoding exon, having a complementary 5' splice acceptor site. A cDNA is synthesized using reverse transcriptase and a mRNA sequence as the template which contains at least the mRNA sequence encoding the Ig V region. This V region-encoding DNA sequence includes a restriction site located on the 5' side of, and adjacent, the junction (VC) of the V region sequence and the flanking sequence encoding a C region. The unique restriction site is chosen to be a specific DNA sequence that is found rarely or only once in the V region DNA, and which is recognized by a particular restriction endonuclease capable of cleaving the DNA at that sequence.

Digestion at the unique restriction site leaves a fragment which encodes at least most of the V region, and preferably defines the 3' end. To the 3' end is ligated an oligodeoxynucleotide referred to herein as a l/a sequence. The l/a sequence includes a DNA portion extending from the VC junction 5'-ward to the restriction site. In addition, the l/a sequence includes at its 3' end a donor splice site which mimics the function of the splice site present in genomic V region-encoding DNA prior to the splicing and rearranging events which occur in the nucleus during mRNA assembly. When ligated together, the restricted V region-encoding cDNA and the l/a sequence form what is referred to herein as a V region cassette.

An appropriate host cell, such as a hybridoma or myeloma, is then transfected with a vector containing the V region cassette and with DNA encoding at least a portion of a polypeptide, such as a C region sequence, which includes a splice acceptor site at its 5' end and a stop signal. The splice acceptor site is compatible with the splice donor site on the 3' end of the V region cassette. The DNA sequence encoding the second polypeptide may be readily retrieved from human genomic libraries. Once isolated, it may be used repeatedly to manufacture Ig having human C regions.

The transfected cell is then cultured to co-express the V region cassette and the C region DNA. A clone which integrates the V region cassette and the C region DNAs splices the separate V and C region DNAs to produce a mRNA encoding a synthetic fused protein comprising the full length V region and a C region or portions thereof. Cotransfection with constructs encoding $V_H$ and $V_L$, suitably introduced in tandem with $C_H$ and $C_L$ sequences, express binding proteins having an authentic Fv domain with binding properties similar to those of the original Ig and C regions from a desired species.

In some embodiments, the resulting polypeptide includes an Ig V region of murine origin and at least a portion of a human C region, thereby forming a chimeric Ig or fragment thereof. The term "chimeric Ig" is used herein to describe an Ig having amino acid sequences derived from Igs of differing specificities and/or different species.

However, it should be appreciated that a given V region or portion thereof may be ligated in this fashion to polypeptides other than Ig C regions to produce chimetic binding molecules other than Ig's. Furthermore, a V region need not be part of the resulting fusion protein at all.

BRIEF DESCRIPTION OF THE DRAWING

The foregoing and other objects and features of the invention, as well as the invention, itself, may be more fully understood from the following description when read together with the accompanying drawings in which:

FIGS. 1A and 1B are schematic representations of the methods of the invention;

FIG. 2 is the nucleic acid sequence and deduced corresponding amino acid sequence of the murine monoclonal 14.18 H chain V region, including a leader sequence, V region, VC junction, and part of a C region;

FIG. 3 is the nucleic acid sequence and deduced corresponding amino acid sequence of the murine monoclonal 14.18 L chain V region, including a leader sequence, V region, VC junction, and part of a C region;

FIGS. 4 panels A–E schematically depict the construction of a representative H chain V region cassette: FIG. 4A is a schematic representation of the murine H chain cDNA including a V and a C region; FIG. 4B is a schematic representation of a V region cassette including the V region cDNA sequence linked at the ScaI site to an I/a DNA sequence comprising a copy of the 3' end of the V region and a splice doner site (ScaI-Hind III); FIG. 4C is the amino acid sequence and corresponding cDNA sequence of a portion of the murine H chain genomic DNA extending from the unique restriction site (here Sca I) in the V region through the VC junction (indicated by a vertical line); FIG. 4D is the nucleic acid sequence of the I/a comprising the portion of the V region sequence extending from the unique restriction site to the VC junction, and including a "universal intron" having a splice donor site adjacent the V region terminus; and FIG. 4E is a schematic representation of the I/a;

FIGS. 5 panels A–E schematically depict the construction of a representative L chain V region cassette: FIG. 5A is a schematic representation of the murine L chain cDNA including a V and C region; FIG. 5B is a schematic representation of a V region cassette including the V region cDNA sequence linked at the Afl III site to an I/a DNA sequence; FIG. 5C is the amino acid sequence and corresponding cDNA sequence of a portion of the murine L chain extending from the unique restriction site (here Afl III) in the V region through the VC junction (indicated by a vertical line); FIG. 5D is the nucleic acid sequence of the I/a comprising the portion of the V region DNA sequence extending from the unique restriction site to the VC junction, and including a "universal intron" having a splice doner site adjacent the V region terminus; and FIG. 5E is a schematic representation of the I/a;

FIGS. 6 panels A–C describe an exemplary cloning strategy for the construction of a chimeric Ig expression vector: FIG. 6A is a schematic representation of the integration of the $V_H$ region cassette (consisting of a $V_H$ cassette and human C region DNA) into a pDEM expression vector; FIG. 6B is a schematic representation of the complete H chain pDEM-VC expression vector including the $V_H$ region cassette and human C region gene; FIG. 6C is a schematic representation of a complete L chain pDEKp-VC expression vector including the $V_L$ region cassette and human C region gene, and demonstrates the location of insertion of the $V_L$ region cassette-human constant region fused DNA sequence into the pDEM-VC vector.

DESCRIPTION OF THE INVENTION

The method of the invention involves the preparation of a polypeptide-encoding cassette including a DNA sequence which enables the splicing of that polypeptide-encoding segment to a second polypeptide-encoding DNA segment having a compatible splice sequence, thereby allowing subsequent transcription and translation of a fusion protein. FIGS. 1 panels A and B schematically describe the methods of the present invention.

In FIG. 1A, a cassette is prepared including the reconstruction of the 3' end of a splice donor (s.d.) site, and its attachment to the 3' end of a DNA sequence or exon encoding a first polypeptide (e.g., toxin, enzyme, lymphokine, interleukin, hormone, growth factor, or Ig domain gene such as a variable (V) region). The cassette is transfected with expressable DNA (structural gene) for a second polypeptide (e.g., growth factor, toxin, enzyme, lymphokine, interleukin, or Ig domain such as a constant (C) region gene) having a compatible splice acceptor (s.a.) site at its 5' end. During the sequence of events leading up to expression in the transfected cell, the two exons are spliced to produce a mature mRNA having a 5' end encoding the first polypeptide, and a 3' end encoding another protein domain, e.g., all or part of a human C region. The resulting single chain polypeptide is a fusion of the first and second polypeptides.

In FIG. 1B, a cassette is prepared including the reconstruction of the 5' end of a splice acceptor site (s.a.), and its attachment to the 5' end of a DNA sequence or exon encoding a first polypeptide (e.g., toxin, enzyme, lymphokine, interleukin, growth factor, or Ig domain such as a constant (C) region). The cassette is cotransfected with expressable DNA (structural gene e.g., a growth factor, toxin, enzyme, lymphokine, interleukin, or Ig domain such as a constant region gene) having a compatible splice acceptor site at its 5' end. During the sequence of events leading up to expression in the transfected cell, the two exons are spliced to produce a mature mRNA having a 3' end encoding the first polypeptide, and a 5' end encoding another protein domain. The resulting single chain polypeptide is a fusion of the first and second polypeptides.

For example, an Ig V region cassette may be spliced to a C region immunoglobulin sequence, resulting in the expression of an intact Ig molecule, an H or L chain, or fragment thereof. Alternatively, a toxin-encoding cassette may be spliced to an Ig V region, resulting in a "magic bullet"-type therapeutic agent.

During the sequence of events leading up to expression in the transfected cell of the fusion protein, mRNA derived from the two DNA sequences are spliced to produce a mature mRNA having a 5' end encoding a complete $V_H$ or $V_L$ and a 3' end encoding another protein domain, e.g., all or part of a human C region. The resulting single chain polypeptide is a fusion of the V region and the polypeptide encoded by the exon of the structural gene. For example, a V region cassette may be spliced to a C region. sequence, resulting in the expression of an Ig molecule, an H or L chain, or fragment thereof.

A representative case includes the construction of a chimeric binding protein such as an antibody. According to the method described in FIG. 1A, an Ig V region cassette is prepared including a reconstruction of the 3' end of the V region and attachment of a splice donor site to the 3' end of a $V_H$- and/or $V_L$-encoding cDNA sequence (first polypeptide). The modified V region cDNA is cotransfected with a structural gene for an Ig constant region (second polypeptide) having a splice acceptor site at its 5' end.

The cDNA encodes a H or L chain V region (most likely non-human, e.g., murine) of a defined specificity, while the C region exon(s) encode the H or L chain C region of another (most likely human) Ig species. Expression of H and L constructs in a single competent host cell results in production of intact chimeric immunoglobulins having a desired specificity and, for example, an intact human constant region. Useful V regions include the $V_H$ and $V_L$ domains of murine monoclonal antibody 14.18 (Mujoo et al. (1987) Cancer Res. 47: 1098–1104) which recognizes the disialoganglioside $G_{D2}$ on the surface of many neuroblastoma, melanoma, glioma, and small lung carcinoma lines and tissues. This V region can be combined with various C regions such as that of the Ig human gamma (H) and kappa (L) chains. Alternatively, the V region may be of human origin.

To produce the V region-containing fused polypeptide, a V region cassette is constructed and placed in an appropriate vector, together with, for example, a C region-encoding DNA sequence.

The V region cassette is constructed as follows. cDNA is synthesized from mRNA isolated from cells rich in V region-encoding mRNA. Useful cell sources include lymphoid cells such as lymphocytes, myelomas and hybridomas. A number of established protocols are available for mRNA isolation and cDNA synthesis (see, e.g., Maniatis et al., ibid.). The longest cDNA molecules are identified, for example, with specific $C_H$ ($C\gamma 3$), $C_L$ ($C\kappa$) sequences, or other nick-translated or oligonucleotide probes in order to detect either or both the L chain or H chain C region. They are then sequenced to identify the DNA sequence of the 3' end of the V region and to locate unique restriction sites within the V region as near as possible to the VC junction.

The next step is to synthesize an oligonucleotide which is used to recreate the sequence between the unique restriction site and splice donor site. In the intact cDNA, the DNA sequence just 5' of the VC junction constitutes the 5' half of the native splice donor site from the genome of the source cell, while the sequence just 3' of the junction (in the C region) represents the 3' half of the native splice acceptor site. The missing portion of each native splice site cannot be deduced from the cDNA since they were removed as part of the introns during mRNA synthesis in the source cell nucleus during the splicing events.

In accordance with the invention, a DNA fragment is synthesized which restores the 3' side of the donor splice site, or alternatively, the 5' side of the acceptor splice site. The fragment should include enough DNA (at least about 80 nucleotide bases) to insure that efficient splicing will occur with an appropriate splice partner sequence. In addition, it is essential that a splice donor/acceptor pair be used that results in a splice maintaining the original reading frame.

To this end, a l/a DNA sequence has been synthesized which includes an intron having parts of its sequence in common with many introns including a splice donor sequence at its 3' end. This universal intron (U) (see FIGS. 1A and B) includes the splice donor sequence GTAATGTG; however, other sequences are equally as useful as splice donors and could be utilized as well. A partial list of exemplary useful splice donor sequences (5' and 3' portions) is shown in TABLE 1. These sequences are from known murine $V_H$ and $V_L$ genomic DNAs. The 5' ends are found at the VC junction of various murine cDNAs, while the 3' ends are removed during the splicing processes. The sequence of the universal intron used herein is also listed for comparison. While the sequences immediately preceding the VC junction should not differ from those shown (since mutations here might lead to RNA splicing problems), it should be mentioned that a 3' portion of the V region in many expressed Ig genes (namely, the J or joining region) undergo somatic mutation. These changes should also be included in the synthetic l/a sequence, since this region may contribute to antigen binding.

TABLE 1

| Murine Ig V(J) Region Splice Donor Sequences | | |
|---|---|---|
| | 5' end | 3' end |
| $J_K1$ | GCTGGAAATCAAAC | GTAAGTAG |
| $J_K2$ | GCTGGAAATAAAAC | GTAAGTAG |
| $J_K3$ | GTTGGAAATAAAAC | GTAAGTAG |
| $J_K4$ | GCTGGAGCTGAAAC | GTAAGTAC |
| $J_H1$ | CACCGTTTCCTCAG | GTAAGCTG |
| $J_H2$ | CACAGTCTCCTCAG | GTGAGTCC |
| $J_H3$ | CACTGTCTCTGCAG | GTGAGTCC |
| $J_H4$ | CACCGTCTCCTCAG | GTAAGAAT |
| (Universal Intron) | | GTAATGTG |

The same universal intron sequences have been used successfully with other V regions. In all cases the Ig L and H chains were efficiently expressed, demonstrating the generality of this process.

Recombinant DNAs comprising a truncated cDNA with restored 3' terminal fragment and donor splice site encoding a first polypeptide and are expressed with another DNA having a splice acceptor site 5' of a region encoding a second polypeptide. For example, a splice acceptor may be derived from genomic Ig DNA encoding all or a portion of an immunoglobulin C region. If a l/a is used which includes a universal intron having a splice acceptor site, any such known splice acceptor site may be incorporated into the sequence. Typically, the 5' end of the splice acceptor site includes a pyrimidine-rich region (i.e., T, C), followed by the sequence AG and the splice junction. Therefore, the universal intron may include such a splice acceptor sequence at its 5' end if the l/a to be used is to be linked to the 5' end of the first DNA sequence instead of the 3' end. Exemplary sequences comprising suitable splice acceptor sites are listed in TABLE 2. These sequences are the acceptor sequences of the: (1) $CH_1$, (2) hinge, (3) $CH_2$, and (4) $CH_3$ exons of the $C\gamma_1$ gene. However, many other suitable splice acceptor sequences can be found in the literature.

TABLE 2

| | 5' end | 3' end |
|---|---|---|
| (1) | CTCTTGCAG | CCTCC |
| (2) | TCTCTGCAG | AGCCC |
| (3) | CTTCCTCAG | CACCT |

TABLE 2-continued

| | 5' end | 3' end |
|---|---|---|
| (4) | GTCCTACAG | GGCAG |

Upon co-expression of the two DNAs, the host cell nuclear enzymes produce mRNA by implementing the normal splicing events, resulting in an mRNA encoding a fused protein. In the case of a chimeric binding protein, the mRNA may encode (5' to 3') a $V_H$ or $V_L$ domain, which may be identical to the native sequence up to the VC junction, attached directly to another polypeptide such as at least a portion of at least one C region domain, which for example, may comprise human sequences. The 3' half of the donor splice site (and any nucleotides downstream) and the 5' half of the acceptor splice site (and any nucleotides upstream) are removed as an intron, resulting in an mRNA encoding the properly fused protein.

Other suitable sources for C-region encloding DNA having an attached 5' splice acceptor site include human or other mammalian genomic libraries. Alternatively, a splice acceptor site having a suitable sequence may be ligated to the 5' end of any desired expressible DNA sequence which may then be fused to a DNA sequence encoding a V domain having a specificity limited only by the specificity of available monoclonal antibodies or those producible by known techniques.

Normally, in the case of chimeric Ig molecules, both exons are placed on the same vector under control of a single regulating sequence. Also, it is preferred to coexpress both L and H chain constructs so that the host cell secretes an intact fusion protein. The method requires use of a host cell having the enzymes which recognize the DNA splice signals and effect proper splicing.

Particular vector construction, host cell selection, transformation, and methods of expression do not, per se, constitute an aspect of the invention, but can be selected and implemented by skilled workers based on personal preference and convenience. Techniques adaptable for use in the invention are disclosed, for example, in *Current Protocols in Molecular Biology* (Greene Publishing Associates, 430 Fourth Street, Brooklyn, N.Y., 1989). Useful vectors include any number of known plasmids which contain the correct signals for transcription and translation of the genes of interest. Enhancer elements may be present, and additional signals for polyadenylation and splicing must be present in cases where they are not provided by the gene itself. For example, all of the signals for the expression of functionally rearranged Ig genes are present on a continuous stretch of DNA and include the transcription promoter, the polyadenylation and termination sites, and the splicing signals for excision of the intron sequences. Additional information that must be provided by the vector is a selectable marker gene. This gene must also contain the signals for expression of the selectable phenotype (usually resistance to the lethal effect of a toxic drug such as methotrexate, for example). Therefore, if the vector encodes both the first and second polypeptides, it is necessary that it provide the sequence information for three separate transcription units in a limited amount of space.

The recombinant cassette-containing vector is transfected into an appropriate host cell. The choice of host cell line, in addition to the criterion noted above, is based on its ability to grow in a growth media, preferably one that is commercially available and serum-free media as well as its ease of selectivity after transformation. For the production of chimeric antibodies, useful host cells include myelomas or hybridomas such as, for example, the murine non-Ig-producing Sp2/0 Ag 14 hybridoma cell line. Useful cells are widely available in repositories and from commercial sources and may be isolated readily from natural sources by those skilled in the art.

One method for introducing recombinant DNA into cells is electroporation (see, e.g., Potter et al. (1984) Proc. Natl. Acad. Sci. USA 81:7161-7165), which requires specialized equipment and the availability of highly purified DNA. However, many different lines can be transformed using this method if conditions are optimized for the specific cell type.

Another transfection method is protoplast (spheroplast) fusion (see, e.g., Sandri-Goldin et al. (1981) Molec. Cell. Biol. 1:743-752). Bacteria harboring the recombinant plasmid of interest are fused to the lymphold cells with a chemical agent, generally 45-50% polyethylene glycol in a buffered, isotonic solution. This method is simple and does not require extensive purification of plasmid DNA. In addition, very high transformation frequencies can be obtained, and the time for obtaining highly productive transfected cell clones is reduced because this transfection method is likely to give transfectants containing multiple copies.

Cells which are successfully transformed with the cassette-containing vector must then be isolated from those which are not. Many methods are available for the selection of transfected cells. For example, the guanine phosphoribosyl transferase (gpt) and neomycin resistance markers may be used for selection purposes in lymphoid cells. The gene encoding the marker would be included on the V-region encoding vector. The resistant form of dihydrofolate reductase (DHFR) can also be used for the selection of hybridoma cell transformants as well as for subsequent amplification of the marker and flanking product genes.

The transfected cell is then cultured to express the polypeptide encoded by the cassette. Culturing may be in vitro, or in the case of recombinant antibodies, may be accomplished by employing other strategies such as in vivo culturing in ascites fluid.

Improvements in the productivity of transfected cells is possible through the use of multiple subcloning steps in the presence of MTX when the sequences of interest are co-expressed with the DHFR marker. For example, after two cycles of subcloning by limiting dilution, cells are obtained that are capable of producing antibody, in spent suspension culture medium, at levels of 35-100 $\mu$g/mL. These levels of expression are greatly reduced if the cells are passaged in the absence of MTX. It is possible, however, to maintain stock cultures in the presence of the drug and then omit it from the last scale-up step. The final yields of antibody in this case are not diminished by the omission of MTX.

In addition to open suspension culture methodologies, other scale-up perfusion technologies such as hollow fiber reactors (see, e.g., Yon Wedel (1987) in *Commercial Production of Monoclonal Antibodies: A Guide for Scale Up* (Seaver, ed.) Marcel Dekker, Inc., New York) and microencapsulation (see, e.g., Rupp (1986) "Use of Cellular Microencapsulation in Large-Scale Production of Monoclonal Antibodies" in *Large Scale Mammalian Cell Culture* (Tolbert and Feder, eds.) Academic Press, New York) are especially useful with the present expression system. For example, it is possible to express high levels of a recombinant human antibody within microcapsules using murine hybridoma transfectants. The entrapped cell cultures can be maintained in medium containing greatly reduced levels of fetal bovine serum, and in some cases, can be maintained in completely serum-free media.

Perfusion methods not only allow for higher cell densities (which may promote cell-cell interactions and thereby reduce the serum requirement), but may also be useful for the removal of MTX from the culture prior to purification of the antibody. This is possible using microencapsulation culture wherein the semipermeable capsule membrane is made to retain the high molecular weight antibody molecule but allow for the diffusion out of the capsule of smaller molecules. At the end of a perfused culture run, long after cell division has stopped but production of antibody continues, the culture could be maintained without MTX. Further removal of the drug is possible by washing and dialyzing the capsules in physiological saline prior to their disruption.

The invention will be further understood from the following non-limiting examples.

EXAMPLE

Two separate H and L chain cDNA libraries are prepared according to the method of Gubler et al. (Gene (1983) 25:263–269), herein incorporated as reference. Double-stranded, blunt-ended cDNA is synthesized from polyadenylated polyA mRNA isolated from the murine hybridoma cell line, 14.18.

A double-stranded polylinker with the sequence:

```
5' HO—AATTCCTCGAGTCGAC
          GGAGCTCAGCTG—PO4 5'
``` is then ligated to the cDNA. This linker serves several purposes. The first allows the blunt-ended cDNA to be cloned into the EcoRI site of λgt10 phage DNA via the AATT sticky-end sequence. Note that only the 5' blunt end has been phosphorylated for ligation to the blunted cDNA. By not phosphorylating the 5' EcoRI sticky end, polymerization of the linkered cDNA does not occur and subsequent enzymatic digestion after linker ligation is unnecessary. This, in turn, makes it unnecessary to methylate internal EcoRI sites which would otherwise be cut in the process. The 5' phosphorylated sticky end provided by the EcoRI digested λgt10 DNA is sufficient for ligation and subsequent cloning of the cDNA in the phage host.

Another function of this linker sequence is to provide XhoI (CTCGAG) and SalI (GTCGAC) sites for subsequent manipulations. These sites rarely occur in murine Ig cDNAs and thus provide unique restriction sites at the 5' and 3' ends. Since both sites provide the same 5' overhang sequence upon restriction (TCGA), either can be used in expression vectors with XhoI cloning sites. If one site happens to appear in the cDNA sequence, the chances are small that the second site would also be present.

The linkered cDNA is then fractionated by polyacrylamide gel electrophoresis (PAGE) to enrich for full-length L and H chain cDNAs. Two fractions of cDNA corresponding to full-length L chain (900–1100 bp) and H chain (1400–1600 bp) can be separately isolated. The DNA in each gel fraction is separately eluted and ligated to EcoRI-digested λgt10 DNA. Following in vitro packaging with commercially available packaging mix (Stratagene, San Diego, Calif.), recombinant phage is plated and screened by filter hybridization using various C region probes.

Ten phage clones from each screening are analyzed further by restriction analysis using ECoRI. This is most rapidly achieved by preparing small-scale phage lysates which provide enough DNA for restriction digest and determination of the length of the cDNA insert. Clones that appear to be full-length are labelled with radioactivity, e.g. at the unique EcoRI sites at the 5' and 3' ends (relative to the original mRNA polarity). Following digestion with a second enzyme, the clones are sequenced by the method of Maxam and Gilbert (Meth. Enzymol. (1980) 65:499–559), herein incorporated by reference, and screened with probes for murine $C\gamma_3$ and $C\kappa$ sequences.

The longest H cDNA sequence is shown in FIG. 2. The H chain clone appears to be very close to full-length if it is assumed that the second ATG in the sequence represents the true initiation codon. Although both ATG codons are in the correct reading frame, the first is probably too close to the 5' end of the mRNA for efficient initiation and, if translated, would encode an uncharacteristically long leader sequence. The use of the second ATG codon would result in the synthesis of a very typical Ig leader sequence of 19 amino acids. Because additional 5' untranslated sequences are to be added to this cDNA in the expression vector (see below), the first ATG would no longer be at the 5' end of the resulting fusion mRNA, thereby increasing the likelihood of the translation of the aberrant leader sequence. To avoid this problem, the cDNA sequence is truncated by limited Bal31 exonuclease treatment. To the resulting modified cDNA clone (H2c) is then attached an XhoI linker (see FIG. 2). The expression of this cDNA should result in an mRNA encoding a normal Ig leader sequence. The remainder of the $V_H$ portion of the cloned cDNA appears to be a normal, functional variable region.

Examination of the L chain clone (FIG. 3) shows a typical L chain sequence encoding a 19 amino acid leader followed by sequences that are highly homologous to the anti-GAT family of $V_\kappa$ genes. The murine $\kappa$ C region begins with the arginine residue at position 114.

Reconstruction of the donor splice sites on the 3' ends of the cloned cDNAs for $V_H$ and for $V_L$ is carried out as shown in FIGS. 4A to E and 5A to E. The first step is to sequence both $V_H$ and $V_L$ regions, and then to identify unique restriction sites near the junctions of the V and C regions (see FIGS. 2 and 3).

The sequence between the unique restriction site and the original splice donor site in the genomic V gene segment is then recreated using the universal intron sequence previously shown in TABLE 1. For convenience, the oligonucleotides used to reconstruct the intron sequence are cloned as a SnaeBl to HindIII fragment (the latter site was not originally part of the intron). The SnaeBl site can then be cut to produce a blunt end beginning with GTA (the bases that reconstitute the splice signal) while the HindIII site serves as the 3' cloning site for insertion of the cassette into the expression vector.

The small linker portions of the V regions shown in panels A–E of FIGS. 4A to E and 5A to E are synthesized by the hybridization and ligation of overlapping oligonucleotides to produce fragments with the appropriate "sticky" 5' end, as well as a blunt 3' end. Each synthetic l/a sequence is then cloned into a plasmid vector for sequence verification. In some cases the 5' cloning site may not be unique or present in a convenient plasmid. In these cases, additional restriction sites can be added to the 5' end of the synthetic DNA for cloning purposes. After DNA sequencing, the l/a fragments are ligated to the remaining portions of the V regions. The complete $V_H$ and $V_K$ region cassettes are then cloned as XhoI to HindIII fragments.

The mammalian cell expression vector used for the expression of the chimeric 14.18 antibody is shown in FIG. 6 panels A–C. It was derived from the pDEM vector (FIG. 6A), which has been used to express cDNA sequences in lymphold cells. This vector was designed as follows. At the left end of the schematic linear representation there is the selectable marker gene, DHFR, which is oriented so that transcription would proceed from right to left. This transcription unit is composed of SV40 regulatory signals (enhancer and promoter), a cDNA encoding the resistant form of mouse DHFR, and an SV40 polyA site.

Adjacent to this gene (to the right of the SalI site) is the transcription unit for the cDNA of interest. The first block of sequence represents the Ig H chain enhancer ($E_\mu$), the sequence that is normally involved in the active transcription of Ig H-chain genes. The enhancer sequence is followed by the promoter for the murine metallothionein (MT) gene. Many other promoters can be used in this position including those from Ig genes, as in the L chain transcription unit shown in FIG. 6C. A synthetic restriction site (for XhoI) is placed in the 5' untranslated region of the MT sequence so that CDNAs can be inserted at this position and be transcribed as fusion mRNAs from the MT promoter. In this case it is necessary that the CDNA contain its own translation initiation codon since it is not provided by the vector. Beyond the XhoI site (after the insertion site for cDNAs) is a segment derived from the 3' untranslated region of the murine $C_K$ region that contains the polyA addition site. A cDNA expressed from this transcription unit would then be composed of the 5' untranslated sequence from the MT mRNA, the specific coding sequence of interest, and the 3' untranslated sequence normally found on murine κ mRNAs.

In the present example of chimeric antibodies, some of the components of this plasmid are superfluous, namely the 3' untranslated sequence and the polyA site from the κ gene segment. Instead of these components, the V region cassette and the human C region gene segment between the XhoI and SalI sites of plasmid pDEM (see FIG. 6A) are inserted. Since the C region gene already provides the 3' untranslated sequences and the polyA site, the only signals to be used from the plasmid are those necessary for the transcription of the cDNA (enhancer and promoter). The resulting plasmid is shown in FIG. 6B.

A similar construct is made for the L chain, but in this case the plasmid has a guanine phosphoribosyltransferase (gpt) selectable marker gene not present in the final vector, and the C region is that of the human κ gene. The promoter used for L chain cDNA expression is derived from a Vκ gene, and a unique XhoI site is placed in the 5' untranslated region for fusion to the cDNA. This latter construct is designed so that the entire L chain transcription unit is flanked by SalI sites, while in the case of the H chain vector, only a single SalI site is retained. In this way it is possible to excise the entire L chain transcription unit (about 3 kb), and then to insert it into the unique SalI site of the H-chain expression vector (FIG. 5C).

Another important design feature of the Ig expression vector involves the use of the $E_\mu$ enhancer for the expression of both H and L chains. Since this enhancer is much more powerful than the L chain counterpart (at least in transfection experiments), a higher and more balanced level of expression of both chains is possible. The L chain transcription unit also contains some additional sequences between the SalI site and the $E_\mu$ sequence. This sequence is derived from the $\lambda_1$ L chain promoter, and serves to attenuate the bi-directional enhancing effect of $E_\mu$ in one direction (away from the L chain transcription unit) without affecting enhancement of transcription of the cDNA (EPO 87/300658.9). When the L chain transcription unit is inserted into the expression vector as shown in FIG. 6 panels A–C, this sequence prevents the overexpression of the adjacent marker gene by blocking the enhancer effect in that direction. In this way it is hoped that transfectants will produce more of the transfected protein of interest relative to the product of the marker gene.

The murine non-Ig-producing hybridoma cell line, Sp2/0 Ag 14 cells are transfected with the chimeric Ig plasmid construct described above using a modified protoplast fusion method (Gillies et al. (1983) Cell 33:717–728), herein incorporated by reference.

After plating in 96-well culture dishes, selection medium (Dulbecco's modified Eagle's medium (DMEM) with 10% fetal bovine serum) containing MTX (0.1 µM) is added. Cells are fed with 50% culture medium replacement at 3–4 day intervals for a total of three feedings. Colonies of MTX-resistant cells appear in 10–14 days.

At this point culture supernatants are assayed for secreted human antibody determinants by an ELISA assay. Nearly all the MTX-resistant colonies secrete significant levels of human antibody into the medium.

After identifying the clones which secrete the most antibody, the expression level is enhanced by increasing the concentration of MTX in the medium. The cells quickly adapt to dramatic increases in concentration (as much as 10-fold in a single step) with little or no cell death. The level of MTX is increased from 0.1 to 10 µM in a period of about three weeks. During this time, the concentration of antibody increases from a range of 2 to 8 µg/mL (at 0.1 µM MTX) to a range of 10 to 40 µg/mL of spent culture medium (at 10 µM MTX). Levels in excess of 100 µg/mL of spent culture medium have been obtained using this and other similar constructs embodying the invention.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method of producing a chimeric antibody having a predetermined specificaity, said method comprising the steps of:
   (a) providing a variable (V) region cassette comprising
       a first nucleic acid having a sequence that encodes a V region having a predetermined specificity, said first nucleic acid being covalently linked through its 3' end to
       a second nucleic acid having a sequence that encodes a splice donor site,
   wherein a portion of the 3' end of said first nucleic acid, together with said second nucleic acid, comprises a synthetic oligonucleotide;
   (b) ligating said V region cassette with a third nucleic acid having a sequence therein that encodes a human immunoglobulin constant (C) region, said third nucleic acid further comprising a 5' splice acceptor site at its 5' end, compatible with said synthetic splice donor site on said V region cassette;
   (c) transfecting said ligated nucleic acid into a eucaryotic host cell, and
   (d) culturing said transfected host cell to produce said chimeric antibody having said predetermined specificity and antigen binding activity.

2. The method of claim 1 wherein said first nucleic acid provided in step (a) encodes an immunoglobulin light chain V region.

3. The method of claim 2 wherein said first nucleic acid encodes a non-human immunoglobulin V region.

4. The method of claim 3 wherein said first nucleic acid encoding an immunoglobulin V region encodes a murine V region.

5. The method of claim 1 wherein said first nucleic acid provided in step (a) encodes an immunoglobulin heavy chain V region.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: miscfeature
      ( B ) LOCATION: 1..22
      ( D ) OTHER INFORMATION: /note="GAP: 14...15
         sequence: Jk1"

( x i ) SEQUENCE DESCRIPTION: SEQ ID NO:1:

GCTGGAAATC AAACGTAAGT AG                     22

( 2 ) INFORMATION FOR SEQ ID NO:2:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: miscfeature
      ( B ) LOCATION: 1..22
      ( D ) OTHER INFORMATION: /note="GAP: 14...15
         sequence: Jk2"

( x i ) SEQUENCE DESCRIPTION: SEQ ID NO:2:

GCTGGAAATA AAACGTAAGT AG                     22

( 2 ) INFORMATION FOR SEQ ID NO:3:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: miscfeature
      ( B ) LOCATION: 1..22
      ( D ) OTHER INFORMATION: /note="GAP: 14...15
         sequence: Jk3"

( x i ) SEQUENCE DESCRIPTION: SEQ ID NO:3:

GTTGGAAATA AAACGTAAGT AG                     22

( 2 ) INFORMATION FOR SEQ ID NO:4:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: miscfeature
      ( B ) LOCATION: 1..22

( D ) OTHER INFORMATION: /note="GAP: 14...15
            Sequence: Jk4"

( x i ) SEQUENCE DESCRIPTION: SEQ ID NO:4:

GCTGGAGCTG  AAACGTAAGT  AC                                              22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 1..22
        ( D ) OTHER INFORMATION: /note="GAP: 14...15
            Sequence: Jh1"

( x i ) SEQUENCE DESCRIPTION: SEQ ID NO:5:

CACCGTTTCC  TCAGGTAAGC  TG                                              22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 1..22
        ( D ) OTHER INFORMATION: /note="GAP: 14...15
            Sequence: Jh2"

( x i ) SEQUENCE DESCRIPTION: SEQ ID NO:6:

CACAGTCTCC  TCAGGTGAGT  CC                                              22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 1..22
        ( D ) OTHER INFORMATION: /note="GAP: 14...15
            Sequence: Jh3"

( x i ) SEQUENCE DESCRIPTION: SEQ ID NO:7:

CACTGTCTCT  GCAGGTGAGT  CC                                              22

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

-continued

```
            ( A ) NAME/KEY: miscfeature
            ( B ) LOCATION: 1..22
            ( D ) OTHER INFORMATION: /note="GAP: 14...15
                    Sequence: Jh4"

( x i ) SEQUENCE DESCRIPTION: SEQ ID NO:8:
```

CACCGTCTCC TCAGGTAAGA AT                                                     22

( 2 ) INFORMATION FOR SEQ ID NO:9:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..8
        ( D ) OTHER INFORMATION: /note="Sequence: Universal
            Intron"

( x i ) SEQUENCE DESCRIPTION: SEQ ID NO:9:

GTAATGTG                                                                      8

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 1..14
        ( D ) OTHER INFORMATION: /note="GAP: 9...10
            Sequence:
            Splice Acceptor 1"

( x i ) SEQUENCE DESCRIPTION: SEQ ID NO:10:

CTCTTGCAGC CTCC                                                              14

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 1..14
        ( D ) OTHER INFORMATION: /note="GAP: 9...10
            Sequence:
            Splice Acceptor 2"

( x i ) SEQUENCE DESCRIPTION: SEQ ID NO:11:

TCTCTGCAGA GCCC                                                              14

( 2 ) INFORMATION FOR SEQ ID NO:12:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: miscfeature
    ( B ) LOCATION: 1..14
    ( D ) OTHER INFORMATION: /note="GAP: 9...10 Splice
        Acceptor 3"

( x i ) SEQUENCE DESCRIPTION: SEQ ID NO:12:

CTTCCTCAGC ACCT                                          14

( 2 ) INFORMATION FOR SEQ ID NO:13:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 1..14
        ( D ) OTHER INFORMATION: /note="GAP: 9...10
            Sequence:
            Splice Acceptor 4"

( x i ) SEQUENCE DESCRIPTION: SEQ ID NO:13:

GTCCTACAGG GCAG                                        14

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 1..16
        ( D ) OTHER INFORMATION: /note="Sequence: Polylinker 5'"

( x i ) SEQUENCE DESCRIPTION: SEQ ID NO:14:

AATTCCTCGA GTCGAC                                  16

( 2 ) INFORMATION FOR SEQ ID NO:15:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 1..12
        ( D ) OTHER INFORMATION: /note="Sequence: Polylinker 5'"

( x i ) SEQUENCE DESCRIPTION: SEQ ID NO:15:

GTCGACTCGA GG                                            12

( 2 ) INFORMATION FOR SEQ ID NO:16:

( i ) SEQUENCE CHARACTERISTICS:
        ( A ) LENGTH: 499 base pairs
        ( B ) TYPE: nucleic acid
        ( C ) STRANDEDNESS: single ( D ) TOPOLOGY: linear ( i i ) MOLECULE TYPE: DNA (genomic)

( i x ) FEATURE:
  ( A ) NAME/KEY: miscfeature
  ( B ) LOCATION: 1..499
  ( D ) OTHER INFORMATION: /note="Leader Sequence: 41...97
    Sequence: 14.18 H Chain"

( x i ) SEQUENCE DESCRIPTION: SEQ ID NO:16:

| | | | | | | |
|---|---|---|---|---|---|---|
| AATGTCCTCT | CCACAGTCCC | TGAAGACACT | GACTATAACT | ATGGGATGGA | CCTGGATCTT | 60 |
| TATTTTAATC | CTGTCGGTAA | CTACAGGTGT | CCACTCTGAG | GTCCAACTGC | TGCAGTCTGG | 120 |
| ACCTGAGCTG | GAGAAGCCTA | GCGCTTCAGT | GATGATATCC | TGCAAGGCTT | CTGGTTCCTC | 180 |
| ATTCACTGGC | TACAACATGA | ACTGGGTGAG | GCAGAACATT | GGAAAGAGCC | TTGAATGGAT | 240 |
| TGGAGCTATT | GATCCTTACT | ATGGTGGAAC | TAGCTACAAC | CAGAAGTTCA | AGGGCAGGGC | 300 |
| CACATTGACT | GTAGACAAAT | CGTCCAGCAC | AGCCTACATG | CACCTCAAGA | GCCTGACATC | 360 |
| TGAGGACTCT | GCAGTCTATT | ACTGTGTAAG | CGGAATGGAG | TACTGGGGTC | AAGGAACCTC | 420 |
| AGTCACCGTC | TCCTCAGCTA | CAACAACAGC | CCCATCTGTC | TATCCCTTGG | TCCCTGGCTG | 480 |
| CAGTGACACA | TCCGGATCC | | | | | 499 |

( 2 ) INFORMATION FOR SEQ ID NO:17:

( i ) SEQUENCE CHARACTERISTICS:
  ( A ) LENGTH: 489 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: miscfeature
  ( B ) LOCATION: 1..489
  ( D ) OTHER INFORMATION: /note="Leader Sequence: 40...96
    Sequence: 14.18 L Chain"

( x i ) SEQUENCE DESCRIPTION: SEQ ID NO:17:

| | | | | | | |
|---|---|---|---|---|---|---|
| CAGTCTCCTC | AGGCTGTCTC | CTCAGGTTGC | CTCCTCAAAA | TGAAGTTGCC | TGTTAGGCTG | 60 |
| TTGGTGCTGA | TGTTCTGGAT | TCCTGCTTCC | AGCAGTGATG | TTGTGATGAC | CCAGACTCCA | 120 |
| CTCTCCCTGC | CTGTCAGTCT | TGGAGATCAA | GCCTCCATCT | CTTGCAGATC | TAGTCAGAGT | 180 |
| CTTGTACACC | GTAATGGAAA | CACCTATTTA | CATTGGTACC | TGCAGAAGCC | AGGCCAGTCT | 240 |
| CCAAAGCTCC | TGATTCACAA | AGTTTCCAAC | CGATTTTCTG | GGGTCCCAGA | CAGGTTCAGT | 300 |
| GGCAGTGGAT | CAGGGACAGA | TTTCACACTC | AAGATCAGCA | GAGTGGAGGC | TGAGGATCTG | 360 |
| GGAGTTTATT | TCTGTTCTCA | AAGTACACAT | GTTCCTCCGC | TCACGTTCGG | TGCTGGGACC | 420 |
| AAGCTGGAGC | TGAAACGGGC | TGATGCTGCA | CCAACTGTAT | CCATCTTCCC | ACCATCCAGT | 480 |
| GAGCAGTTA | | | | | | 489 |

( 2 ) INFORMATION FOR SEQ ID NO:18:

( i ) SEQUENCE CHARACTERISTICS:
  ( A ) LENGTH: 57 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 1..57
  ( D ) OTHER INFORMATION: /note="Splice Site: 43...44

Sequence: H Chain VC Junction"

( x i ) SEQUENCE DESCRIPTION: SEQ ID NO:18:

| ATG | GAG | TAC | TGG | GGT | CAA | GGA | ACC | TCA | GTC | ACC | GTC | TCC | TCA | GCT | ACA | 48 |
|-----|-----|-----|-----|-----|-----|-----|-----|-----|-----|-----|-----|-----|-----|-----|-----|----|
| Met | Glu | Tyr | Trp | Gly | Gln | Gly | Thr | Ser | Val | Thr | Val | Ser | Ser | Ala | Thr |    |
| 1   |     |     | 5   |     |     |     | 10  |     |     |     | 15  |     |     |     |     |    |

| ACA | ACA | GCC |   | 57 |
|-----|-----|-----|---|----|
| Thr | Thr | Ala |   |    |

( 2 ) INFORMATION FOR SEQ ID NO:19:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| Met | Glu | Tyr | Trp | Gly | Gln | Gly | Thr | Ser | Val | Thr | Val | Ser | Ser | Ala | Thr |
|-----|-----|-----|-----|-----|-----|-----|-----|-----|-----|-----|-----|-----|-----|-----|-----|
| 1   |     |     | 5   |     |     |     | 10  |     |     |     | 15  |     |     |     |     |

Thr Thr Ala ( 2 ) INFORMATION FOR SEQ ID NO:20:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: 52..53
        ( D ) OTHER INFORMATION: /note="Splice Site: 40...41
        GAP: 52...53 Sequence: H Chain 1/a"

( x i ) SEQUENCE DESCRIPTION: SEQ ID NO:20:

```
GAGTACTGGG GTCAAGGAAC CTCAGTCACC GTCTCCTCAG GTAAGTGTGT CAGGTAATGT    60

CACTAAGCTT                                                           70
```

( 2 ) INFORMATION FOR SEQ ID NO:21:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..66
        ( D ) OTHER INFORMATION: /note="Splice Site: 52...53
        Sequence: L Chain VC Junction"

( x i ) SEQUENCE DESCRIPTION: SEQ ID NO:21:

| ACA | CAT | GTT | CCT | CCG | CTC | ACG | TTC | GGT | GCT | GGG | ACC | AAG | CTG | GAG | CTG | 48 |
|-----|-----|-----|-----|-----|-----|-----|-----|-----|-----|-----|-----|-----|-----|-----|-----|----|
| Thr | His | Val | Pro | Pro | Leu | Thr | Phe | Gly | Ala | Gly | Thr | Lys | Leu | Glu | Leu |    |
| 1   |     |     | 5   |     |     |     | 10  |     |     |     | 15  |     |     |     |     |    |

| AAA | CGG | GCT | GAT | GCT | GCA |   | 66 |
|-----|-----|-----|-----|-----|-----|---|----|
| Lys | Arg | Ala | Asp | Ala | Ala |   |    |
|     |     | 20  |     |     |     |   |    |

( 2 ) INFORMATION FOR SEQ ID NO:22:

( i ) SEQUENCE CHARACTERISTICS:

(A) LENGTH: 22 amino acids
            (B) TYPE: amino acid
            (D) TOPOLOGY: linear (ii) MOLECULE TYPE: protein (xi) SEQUENCE DESCRIPTION: SEQ ID NO:22:

Thr His Val Pro Pro Leu Thr Phe Gly Ala Gly Thr Lys Leu Glu Leu
1               5                   10                  15

Lys Arg Ala Asp Ala Ala
            20

(2) INFORMATION FOR SEQ ID NO:23:

(i) SEQUENCE CHARACTERISTICS:
            (A) LENGTH: 77 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: miscfeature
            (B) LOCATION: 1..77
            (D) OTHER INFORMATION: /note="Splice Site: 50...51
                GAP: 59...60 Sequence: L Chain 1/a"

(xi) SEQUENCE DESCRIPTION: SEQ ID NO:23:

ACACGTTCCT CCGCTCACGT TCGGTGCTGG GACCAAGCTG GAGCTGAAAC GTAAGTGTGG    60

GTAATGTCAC TAAGCTT                                                   77